United States Patent
Alam et al.

(10) Patent No.: US 10,940,088 B1
(45) Date of Patent: Mar. 9, 2021

(54) METHOD OF PREPARING LOW DOSE PHARMACEUTICAL FORMULATIONS

(71) Applicant: KING SAUD UNIVERSITY, Riyadh (SA)

(72) Inventors: Mohd Aftab Alam, Riyadh (SA); Fahad Ibrahim Al-Jenoobi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/738,566

(22) Filed: Jan. 9, 2020

(51) Int. Cl.
*A61J 3/07* (2006.01)
*A61K 9/08* (2006.01)
*A61K 9/48* (2006.01)

(52) U.S. Cl.
CPC ............... *A61J 3/074* (2013.01); *A61J 3/072* (2013.01); *A61K 9/08* (2013.01); *A61K 9/4883* (2013.01)

(58) Field of Classification Search
None
See application file for complete search history.

(56) References Cited

U.S. PATENT DOCUMENTS

| | | | |
|---|---|---|---|
| 4,231,211 A * | 11/1980 | Strampfer | A61J 3/074 53/452 |
| 4,497,158 A * | 2/1985 | Durr | A61J 3/074 424/452 |
| 6,746,438 B1 | 6/2004 | Arnissolle | |
| 7,560,429 B2 | 7/2009 | Nilsson et al. | |
| 2001/0036472 A1 * | 11/2001 | Wong | A61K 9/0004 424/456 |
| 2016/0175246 A1 * | 6/2016 | Nilsson | A61P 13/10 514/6.9 |

FOREIGN PATENT DOCUMENTS

JP 2017002090 A 1/2017

OTHER PUBLICATIONS

Paudel et al., "Manufacturing of solid dispersions of poorly water soluble drugs by spray drying:Formulation and process considerations", International Journal of Pharmaceutics 453 (2013) 253-284. (Year: 2013).*
Augsburger, Larry L., (2007) "Hard Shell Capsules". Food Machinery Corporation (FMC).
Birchall, J. C., Jones, B. E., Morrissey, A., & Jones, B. E. (2008). A comparison of the puncturing properties of gelatin and hypromellose capsules for use in dry powder inhalers. Drug development and industrial pharmacy, 34(8), 870-876.
Kukker, V., Anand, V., Kataria, M., Gera, M., & Choudhury, P. K. (2008). Mixing and formulation of low dose drugs: underlying problems and solutions. Thai J Pharms Sci, 32(3-4), 43-58.

* cited by examiner

*Primary Examiner* — Melissa L Fisher
(74) *Attorney, Agent, or Firm* — Nath, Goldberg & Meyer; Richard C. Litman

(57) ABSTRACT

Low dose pharmaceutical formulations may be prepared to deliver consistent low doses of a variety of pharmaceuticals with minimal additives. In particular, the low dose pharmaceutical formulations are solid unit dosage forms of low dose drug substances which may be prepared by a method that provides content uniformity across prepared solid unit dosage forms.

7 Claims, 10 Drawing Sheets

METHOD OF PREPARING LOW DOSE PHARMACEUTICAL FORMULATIONS

BACKGROUND

1. Field

The present invention relates to low dose pharmaceutical formulations and methods of preparing the low dose pharmaceutical formulations.

2. Description of the Related Art

Many high potency drugs must be administered in low dose formulations. However, it is difficult for formulation scientists to prepare low dose solid unit dosage forms with acceptable content uniformity. For solid unit dosage forms (e.g., tablets, capsules), the active substance should be distributed uniformly in the unit dosage forms and the active substance should also be dissolvable. It is challenging to achieve content uniformity in low dose solid formulations because uniform mixing of formulation components is difficult and segregation of mixed components often occurs during handling. As a result, in such cases the content of the solid unit dosage forms will not be uniform. Content uniformity is one of the key quality parameters for solid unit dosage forms. Significant deviations in the content of drug substance in solid unit dosage forms may impact the quality, safety, and efficacy of the unit dosage form.

Conventional approaches to prevent de-mixing or to maintain content uniformity in low dose solid formulations may involve additional processing steps or additives that may further require extensive quality control work.

Accordingly, low dose pharmaceutical formulations and methods of preparing low dose pharmaceutical formulations solving the above problems are desired.

SUMMARY

As described herein, low dose pharmaceutical formulations with acceptable content uniformity may be prepared by adding an active drug substance in solution directly to a capsule body. The present method avoids the content non-uniformity caused by de-mixing or non-uniform mixing of active drug substance and or solid pharmaceutical excipients. The low dose pharmaceutical formulations prepared by the methods described herein require minimal pharmaceutical excipients.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
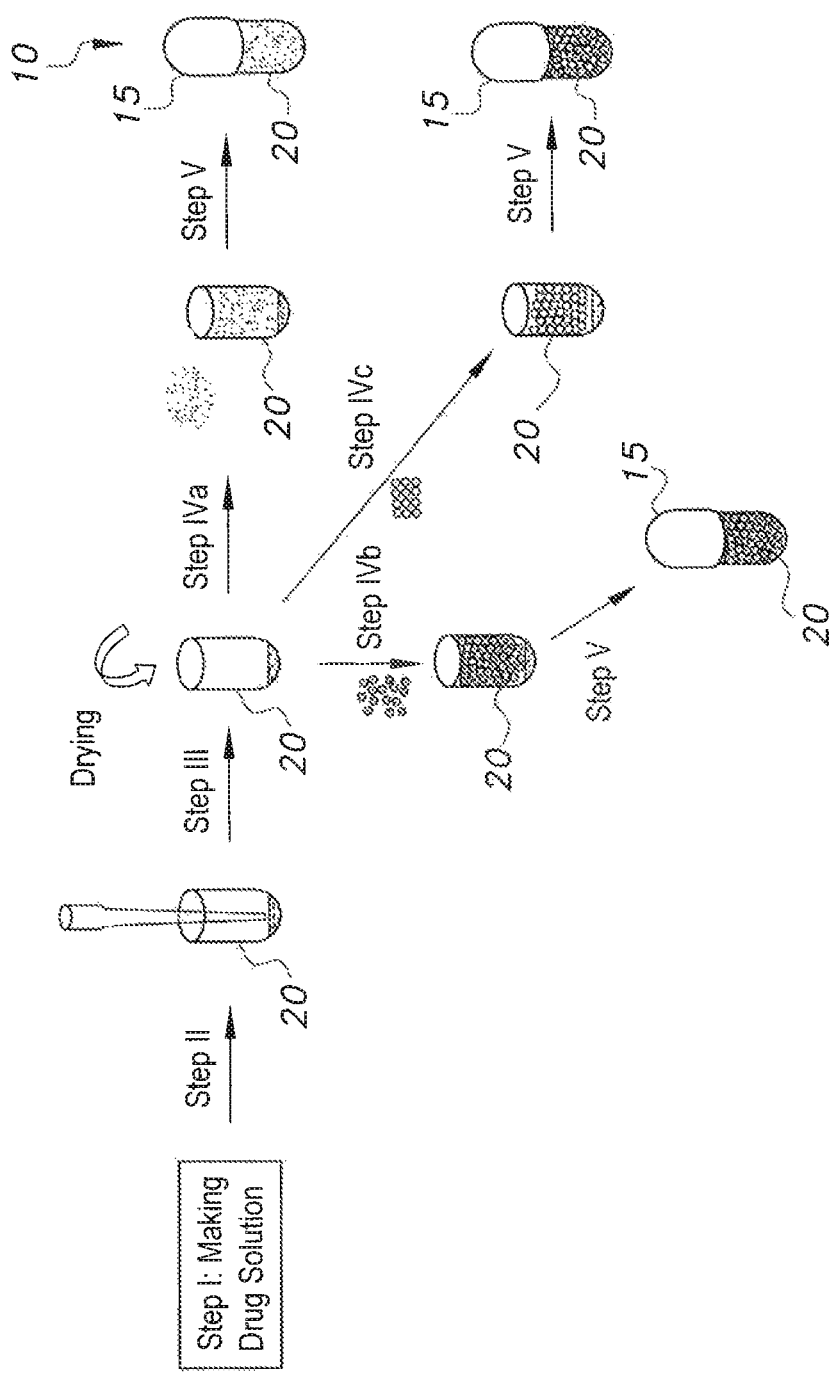
FIG. 1 is a flow diagram of a method for preparing low dose pharmaceutical formulations according to one embodiment of the present subject matter.

A method of preparing low dose pharmaceutical formulations includes providing an empty capsule shell having a capsule body with an opening at one end and a capsule cap for covering the opening of the capsule body; providing a drug solution comprising a solvent and a drug; and transferring the drug solution directly into the body of the capsule shell. In an embodiment, the drug solution can be transferred into the capsule body when the opening is exposed. In an embodiment, the drug solution can be transferred into the capsule body when the opening is covered with the capsule cap. The opening of the capsule body can be covered with the capsule cap, e.g., by at least partially inserting the capsule body into the capsule cap. In some embodiments, the capsule shell is a hard gelatin shell or a HPMC capsule shell. The drug can be a low dose active drug substance as described in detail herein.

In an embodiment, the solvent of the drug solution may be removed once the drug solution is dispensed in the capsule body. In an embodiment, the capsule body may be filled with non-therapeutic material before the drug solution is dispensed in the capsule body. In an embodiment, the capsule body may be filled with non-therapeutic material after the drug solution is dispensed in the capsule body. The solvent of the drug solution may be removed under a nitrogen stream, or under an air stream, or by leaving the capsule body uncovered and allowing the drug solution to be exposed to room temperature.

The non-therapeutic material can include a material which is safe for oral use and does not have any significant adverse effects or therapeutic effect on a human body in the amount provided in the unit dosage form.

According to an embodiment, the non-therapeutic material can include at least one of pharmaceutical excipients, food grade ingredients, and other inert and safe materials that are absorptive and/or adsorptive.

In an embodiment of the present method, the non-therapeutic material may be in the form of a powder, or placebo granules, or sugar spheres, or a fiat disc, or a strip.

In one embodiment of the present method, the drug solution is transferred into a capsule body while the capsule body is open, and the solvent of the drug solution is then removed from the capsule body. After solvent removal, the capsule body is closed by covering the opening of the capsule body with the capsule cap. The non-therapeutic material may be added to the capsule body before or after the drug solution is dispensed in the capsule body. The non-therapeutic material may be added to the capsule body before or after solvent removal. In an embodiment, the non-therapeutic material is added to the capsule body before covering the capsule body with the capsule cap. More than one non-therapeutic material may be added. For example, a first non-therapeutic material may be a carrier element such as a flat disc or strip that is placed in the capsule body after the drug solution is transferred to the capsule body. After the flat disc or strip is placed in the capsule body, a second non-therapeutic material may be added. The carrier element can have adsorptive and/or absorptive properties.

In another embodiment of the present method, the drug solution is transferred into the capsule body while the opening of the capsule body is covered by the cap. In this embodiment, the drug solution is injected into the capsule shell. The capsule shell may be empty when the drug solution is injected therein, or the capsule shell may be prefilled with one or more non-therapeutic materials. The injection site of the capsule may be sealed following injection, for example, by using a sealant selected from a viscous solution of gelatin, hydroxypropyl methylcellulose, carboxymethyl cellulose, sodium carboxymethyl cellulose, hydroxypropyl cellulose, swollen viscous gelling compositions of natural gums (e.g., gum acacia, guar gum and xantham gum) or a solution of film forming polymers. For example, a small droplet of the sealant may be placed over the injection site.

The pharmaceutical excipient can be selected from diluents, disintegrants, binders, buffering agents, acidifying agents, alkalizing agents, glidants, lubricants, color, sweeteners, anti-oxidants, preservatives, desiccants, viscosity enhancers, and solubilizers.

The diluent can be selected from mannitol, lactose monohydrate, lactose anhydrous, microcrystalline cellulose, alpha-cyclodextrin, beta-cyclodextrin, gama-cyclodextrin, hydropropyl beta-cyclodextrin, maltitol, maltodextrin, maltose, sorbitol, dibasic calcium phosphate, tribasic calcium phosphate, calcium sulfate dihydrate, calcium carbonate, powdered cellulose, dextrates, fructose, lactitol, corn starch, potato starch, wheat starch, pregelatinized starch, tapioca starch, compressible sugar, sucrose, and confectioner's sugar.

The disintegrant can be selected from crospovidone, croscarmellose sodium, low-susbstituted hydroxypropylcellulose, sodium starch glycolate, microcrystalline cellulose, polacrilin potassium, corn starch, potato starch, tapioca starch, and wheat starch.

The binder can be selected from acacia, ethylcellulose, gelatin, carboxymethylcellulose sodium, methylcellulose, dextrin, maltodextrin, syrup, date syrup, xanthan gum, guar gum, hydroxypropyl methyxellulose (HPMC), hydroxypropylcellulose, maltose, povidone, corn starch, tapioca starch, wheat starch, potato starch, and pregelatinized starch.

The buffering agents can be selected from lactic acid, citric acid monohydrate, citric acid anhydrous, potassium citrate, sodium citrate, succinic acid, acetic acid, sodium acetate, adipic acid, ammonium phosphate, ammonium carbonate, boric acid, phosphoric acid, potassium metaphosphate, potassium phosphate dibasic, potassium phosphate monobasic, sodium lactate, sodium phosphate dibasic, and sodium phosphate monobasic.

The acidifying agents can be selected from citric acid anhydrous, citric acid monohydrate, malic acid, fumaric acid, tartaric acid, acetic acid, glacial acetic acid, hydrochloric acid, and phosphoric acid.

The alkalizing agent can be selected from sodium bicarbonate, sodium borate, sodium carbonate, sodium hydroxide, potassium hydroxide, strong ammonia solution, ammonium carbonate, diethanolamine, and trolamine.

The glidant can be selected from talc, colloidal silicon dioxide, calcium silicate, and magnesium silicate.

The lubricant can be selected from magnesium stearate, calcium stearate, glyceryl behenate, light mineral oil, sodium lauryl sulfate, sodium stearyl fumarate, stearic acid, and talc.

The color can be selected from ferric oxide red and ferric oxide yellow.

The sweetener can be selected from mannitol, dextrose, fructose, sorbitol, sucralose, compressible sugar, confectioner's sugar, acesulfame potassium, aspartame, dextrates, galactose, maltitol, maltose, saccharine, saccharine calcium, and saccharine sodium.

The antioxidant can be selected from potassium metabisulfite, sodium bisulfite, sodium formaldehyde sulfoxylate, sodium metabisulfite, sodium thiosulfate, ascorbic acid, ascorbyl palmitate, tocopherol, butylated hydroxyanisol, and butylated hydroxytoluene.

The preservative can be selected from propylparaben, propylparaben sodium, butylparaben, ethylparaben, methylparaben, methylparaben sodium, sodium benzoate, sorbic acid, potassium sorbate, benzalkonium chloride, benzethonium chloride, benzoic acid, and potassium benzoate.

The desiccant can be selected from silicon dioxide, calcium chloride, and calcium sulfate.

The solubilizing agent or emulsifying agent can be selected from sodium lauryl sulfate, docusate sodium, polysorbate 60, polysorbate 80, sorbitan monolaurtae, sorbitan monooleate, sorbitan monopalmitate, sorbitan monostearate and sorbitan trioleate.

The suspending or viscosity enhancing agent can be selected from dextrin, gelatin, gellan gum, guar gum, tragacanth, xanthan gum, gum acacia, agar, bentonite, carbomer 910, carbomer 934, carbomer 934p, carbomer 940, carboxymethylcellulose, carboxymethylcellulose sodium, hydroxyethyl cellulose, hydroxypropyl cellulose, hydropropyl methycellulose, polyvinyl alcohol, povidone, sodium alginate, corn starch, wheat starch, potato starch, and tapioca starch.

The solvent or vehicle can be selected from water, ethanol, water-ethanol mixture, acidic or alkaline aqueous medium, methanol, propanol, butanol, acetone, and dimethyl sulfoxide (DMSO).

The placebo granules can include one or more suitable pharmaceutical excipients described herein and can be prepared using state of the art methods, such as wet granulation, or dry granulation, or direct compression.

The carrier element may be a flat disc shape or a strip. The flat, disc-shaped carrier element may have a circular or angular (e.g., square, rectangular, triangular) periphery. The strip may be flat, folded length wise and/or width-wise, or rolled. The carrier element may have the shape of a stick, rod, hollow cylinder, or sphere.

In an embodiment, the amount of active substance in low dose pharmaceutical formulations is equal to or less than 2 mg. In an embodiment, the amount of active substance in the low dose pharmaceutical formulation is less than 2% (w/w) of the total weight of the composition.

The low dose active drug substance can be selected from the following examples or from the corresponding pharmaceutically acceptable salts or esters: alprazolam, atropine methionitrate, atropine sulphate, amlodipine besilate, anagrelide, aripiprazole, amitriptyline hydrochloride, anastrozole, alendronate sodium, alfacalcidol, adefovir dipivoxil, betamethasone, baclofen, budesonide, bisacodyl, bisoprolol fumarate, bromhexine hydrochloride, buprenorphine, betahistine dihydrochloride, benztropine mesylate, biotin, benzhexol hydrochloride, bromocriptine, busulfan, clonidine hydrochloride, colchicine, chlorpheniramine maleate, clomipramine hydrochloride, carvedilol, chlorambucil, carbimazole, clonazepam, cabergoline, calcitriol, cyproterone acetate, candesartan, cetirizine, dienoestrol, digitoxin, digoxin, desmopressin acetate, diazepam, domperidone, doxepin, dexamethasone, dydrogesterone, distigmine bromide, ergometrine maleate, escitalopram, ergotamine tartarate, entecavir, estradiol valerate, ethinyl estradiol, enalapril maleate, fludrocortisone acetate, felodipine, finasteride, folic acid, glimepiride, glibenclamide, glipizide, granisetron, hyoscine butylbromide, hydroxyzine, haloperidol, hydrocortisone, isosorbide dinitrate, ivabradine, ivermectin, imipramine hydrochloride, indapamide, loperamide hydrochloride, lorazepam, levothyroxine sodium, lornoxicam, letrozole, liothyronine t3, loratadine, methylergometrine maleate, metolazone, metoprolol tartrate, methylphenidate, metoclopramide hydrochloride, morphine sulfate, methadone hydrochloride, montelukast sodium, menadiol sodium phosphate, meloxicam, melphalan, methotrexate, misoprostol, methylergonovine maleate, memantine hydrochloride, medroxyprogesterone acetate, methoxsalen, norgestrel, nitroglycerin, nicotine, nitrazepam, norethisterone, olanzapine, ondansetron, oxybutynin hydrochloride, prazosin hydrochloride, perindopril, pramipexole, procyclidine hydrochloride, paliperidone, phenobarbital, primaquine phosphate, prednisolone, phytomenadione, promethazine hydrochloride, pyridoxine hydrochloride, risperidone, rosuvastatin, repaglinide, sirolimus, sodium aurothiornalate, simvastatin, sennosides, selegiline hydrochloride, tacrolimus, tamoxifen citrate, tamsulosin hydrochloride, tolterodine tartrate, thyroxine sodium, tropisetron, trifluoperazine hydrochloride, varenicline, warfarin sodium, zuclopenthixol and zolpidem tartrate.

METHODS OF PREPARING LOW DOSE PHARMACEUTICAL FORMULATION

Method-I

A first embodiment of preparing a low dose pharmaceutical formulation (herein, "Method-I") is illustrated in FIG. 1. Method-I includes five steps:

Step-I: Dissolving the drug substance in a suitable vehicle to create a drug solution;

Step-II: Transferring the required volume of drug solution into an empty capsule body 20;

Step-III: Removing the solvent of the drug solution (e.g., drying) from the capsule body 20 either at room temperature or by using a nitrogen gas stream or by using an air stream;

Step-IV: After drying, filling the capsule body with at least one non-therapeutic material selected from:
   (a) pharmaceutical excipients,
   (b) placebo granules, and
   (c) sugar spheres; and Step-V: After filling, closing the capsule body 20 by using a capsule cap 15 to provide a capsule.

Figure 2:
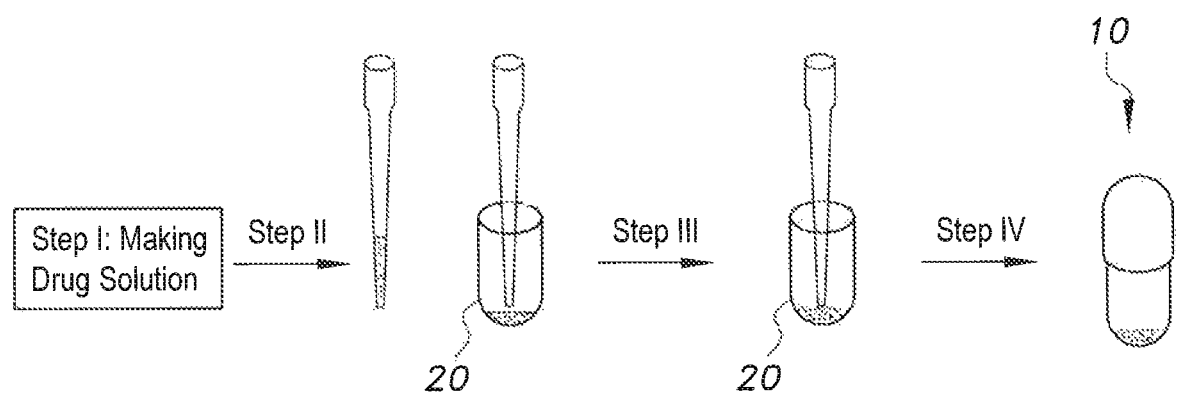
FIG. 2 is a flow diagram of a method for preparing low dose pharmaceutical formulations according to another embodiment of the present subject matter.

Method-II:

Method-II is illustrated in FIG. 2. Method-II includes four steps:

Step-I: Dissolving the drug substance in a suitable vehicle to create a drug solution;

Step-II: Transferring the required volume of drug solution into an empty capsule body 20;

Step-III: Removing the solvent of drug solution (drying) from the capsule body 20 either at room temperature or by using a nitrogen gas stream or by using an air stream; and Step-IV: After drying, closing the capsule body 20 by using a capsule cap 15.

Method-III

Figure 3:
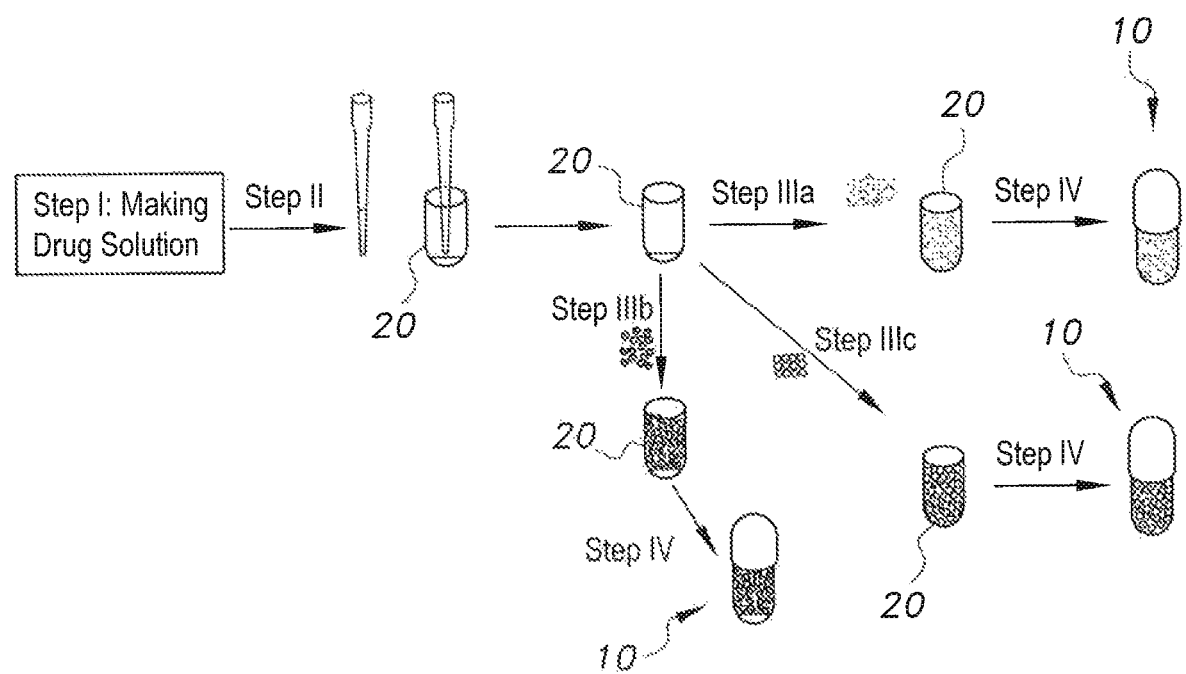
FIG. 3 is a flow diagram of a method fix preparing low dose pharmaceutical formulations according to another embodiment of the present subject matter.

Method-III is illustrated in FIG. 3. Method-III includes four steps:

Step-I: Dissolving the drug substance in a suitable vehicle to create a drug solution;

Step-II: Transferring the required volume of drug solution into an empty capsule body 20;

Step-III: Filling the capsule body 20 with at least one non-therapeutic material selected from:
   (a) pharmaceutical excipients,
   (b) placebo granules, and
   (c) sugar spheres; and Step-V: After filling, closing the capsule body 20 by using capsule cap 15.

Method-IV

Figure 4:
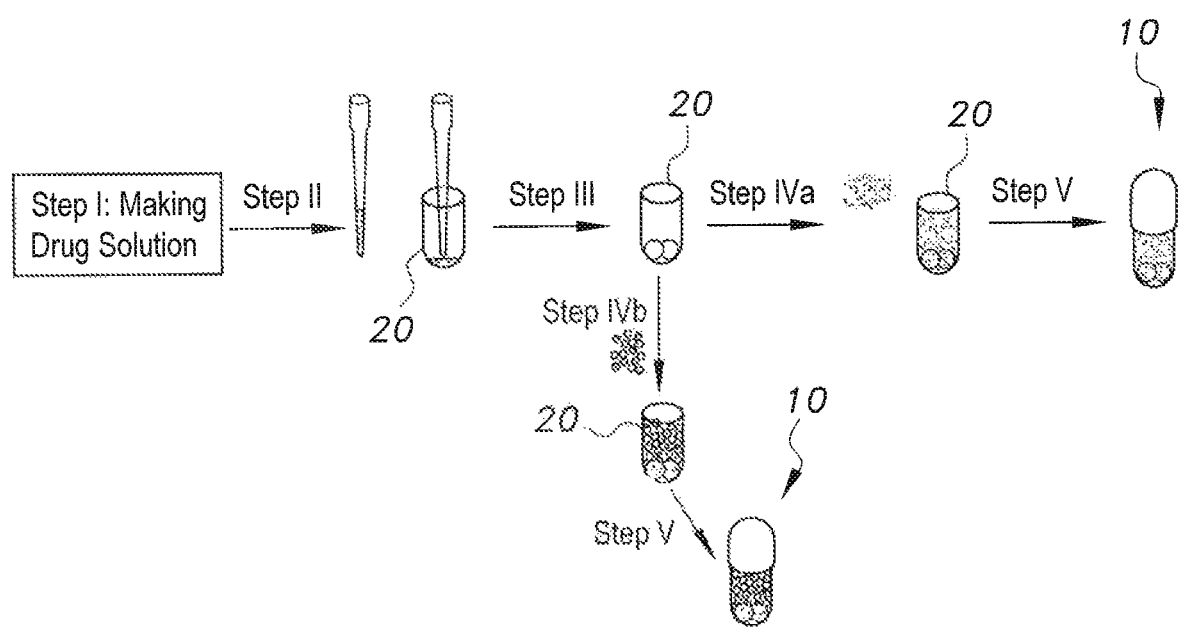
FIG. 4 is a flow diagram of a method for preparing low dose pharmaceutical formulations according to another embodiment of the present subject matter.

Method-IV is illustrated in FIG. 4. Method-IV includes four or five steps:

Step-I: Dissolving the drug substance in a suitable vehicle to create a drug solution;

Step-II: Transferring the required volume of drug solution into empty capsule body 20;

Step-III: Filling at least one non-therapeutic material (carrier element) in capsule body 20, and Step-IV: Optionally filling another non-therapeutic material in capsule body 20, selected from:
   (a) pharmaceutical excipients,
   (b) placebo granules,
   (c) sugar spheres, and Step-V: After filling, closing the capsule body 20 by using capsule cap 15.

The carrier elements, e.g., carrier disk, in an exemplary implementation of Method-IV can be made from Whatman® filter paper (Grade 3), as illustrated in FIG. 4. The horizontal dimensions (diameter, or width and length) of the carrier element are preferably configured to fit in the capsule body without folding. If a larger size carrier element is required for drug loading, then a folded carrier element can be used. The carrier element has uniform thickness all through its surface. The thickness of the carrier disc can be between 0.1 mm-2 mm. Preferably, the thickness of the carrier element can be between 0.2 mm-1 mm. In an embodiment, the carrier disc is formed from Whatman® filter paper (Grade 3), using a hole puncher. The flat, strip-shaped carrier element can have a length that is at least double of its width. The thickness of the strip-shaped carrier strip can be between 0.1 mm-2 mm. Preferably the thickness of the strip-shaped carrier strip can be between 0.2 mm-1 mm. The carrier element can be folded at its width or at its length. The carrier element can be rolled spirally or concentrically.

Method-V

Figure 5:
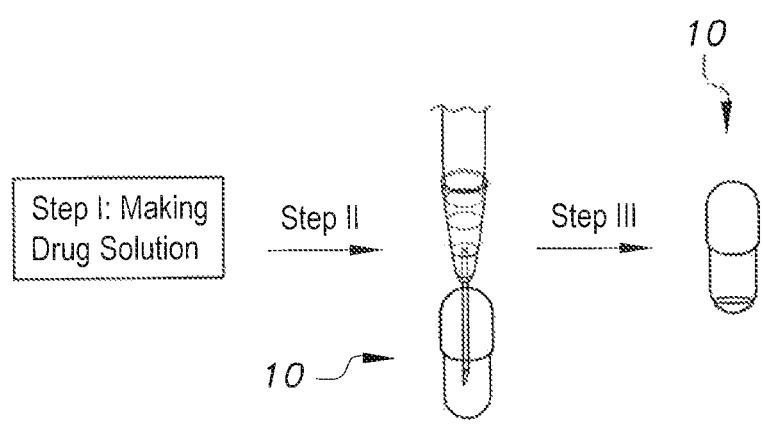
FIG. 5 is a flow diagram of a method for preparing low dose pharmaceutical formulations according to another embodiment of the present subject matter.

Method-V is illustrated in FIG. 5. Method-V includes two or three steps:
- Step-I: Dissolving the drug substance in a suitable vehicle to create a drug solution;
- Step-II: Injecting the required volume of drug solution into an empty closed capsule shell; and
- Step-III: Optionally sealing the injection site.

Method-VI

Figure 6:
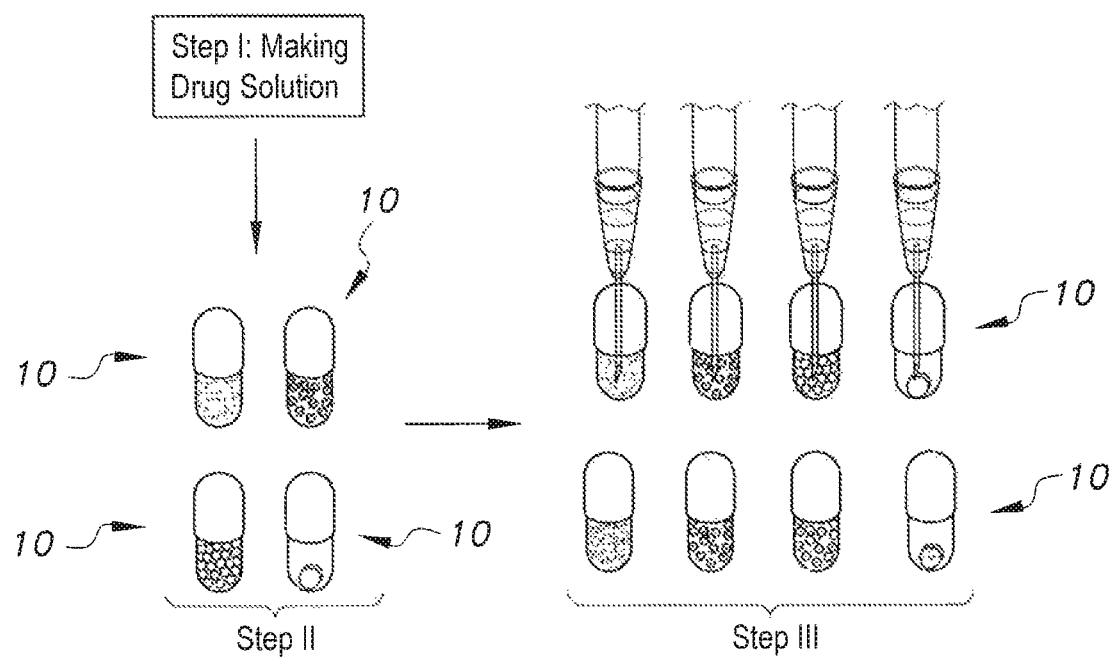
FIG. 6 is a flow diagram of a method for preparing low dose pharmaceutical formulations according to another embodiment of the present subject matter.

Method-VI is illustrated in FIG. 6. Method-VI includes three or four steps:
- Step-I: Dissolving the drug substance in a suitable vehicle to create a drug solution;
- Step-II: Filling non-therapeutic material into the capsule shell;
- Step-III: Injecting the required volume of drug solution into non-therapeutic material filled in capsule shell; and
- Step-IV: Optionally sealing the injection site.

Method-VII

Figure 7:
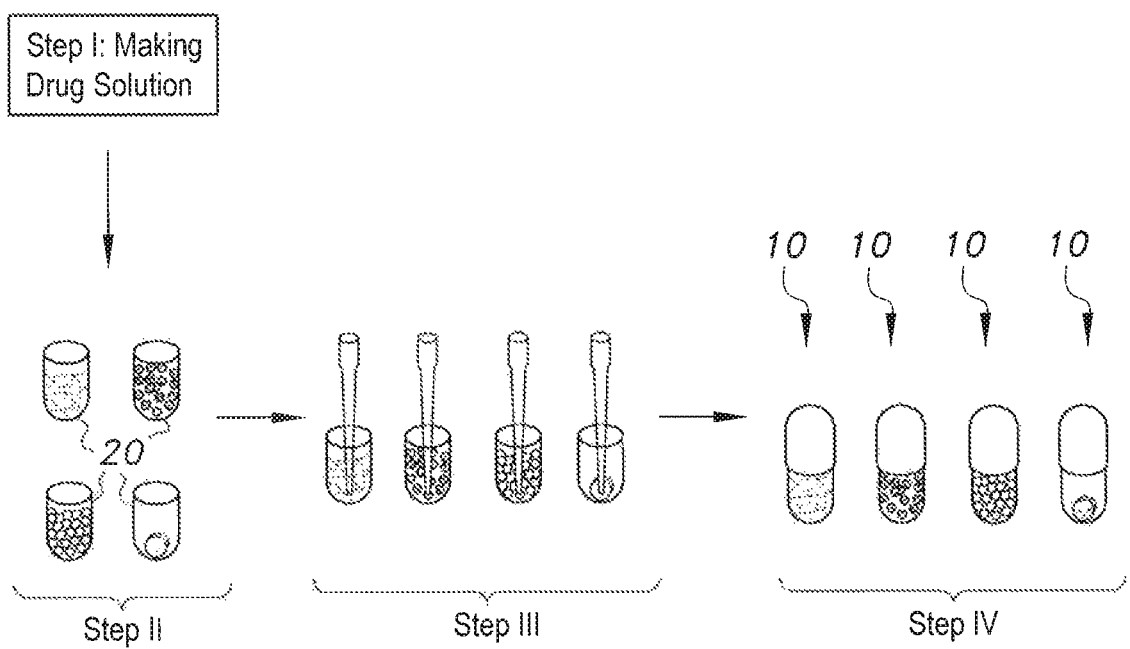
FIG. 7 is a flow diagram of a method for preparing low dose pharmaceutical formulations according to another embodiment of the present subject matter.
Figure 8:
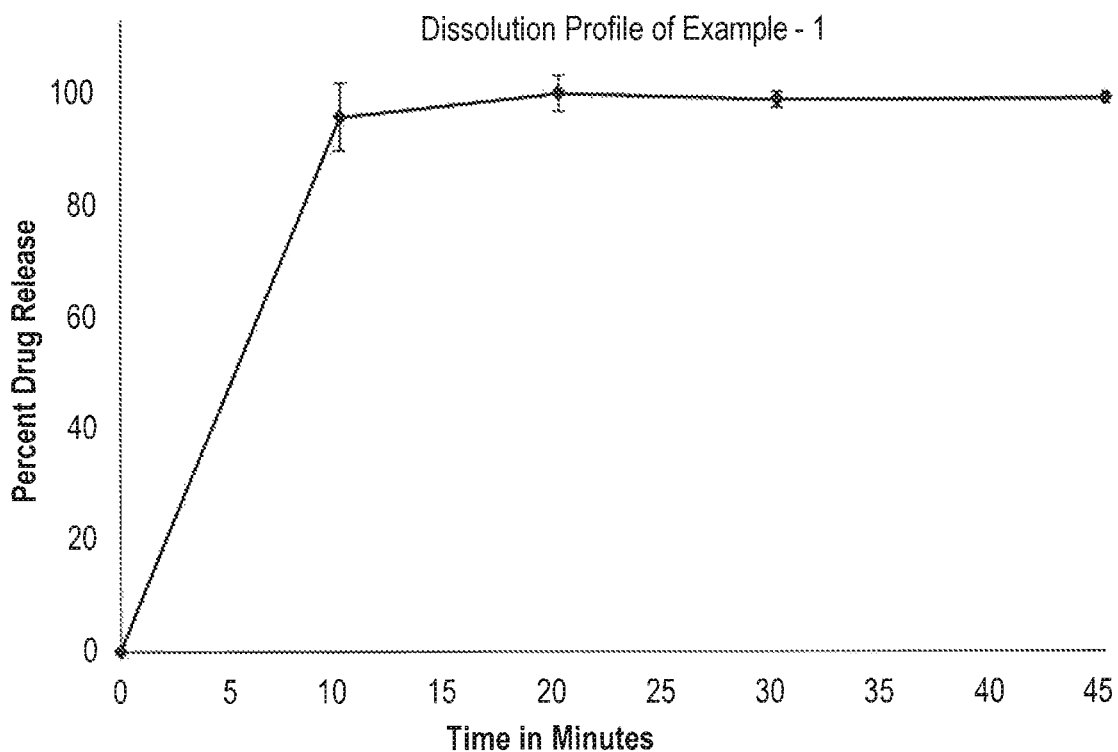
FIG. 8 is a graph illustrating the mean dissolution profile of formulations prepared in accordance with Example 1.
Figure 9:
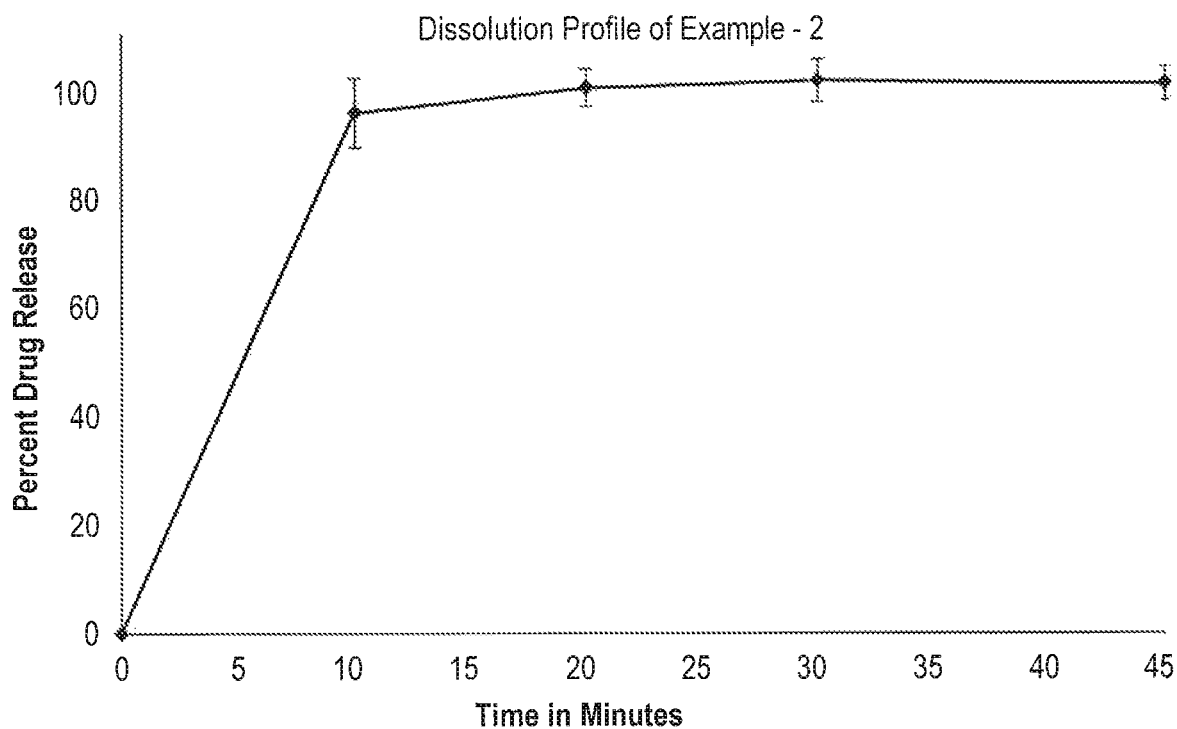
FIG. 9 is a graph illustrating the mean dissolution profile of formulations prepared in accordance with Example 2.
Figure 10:
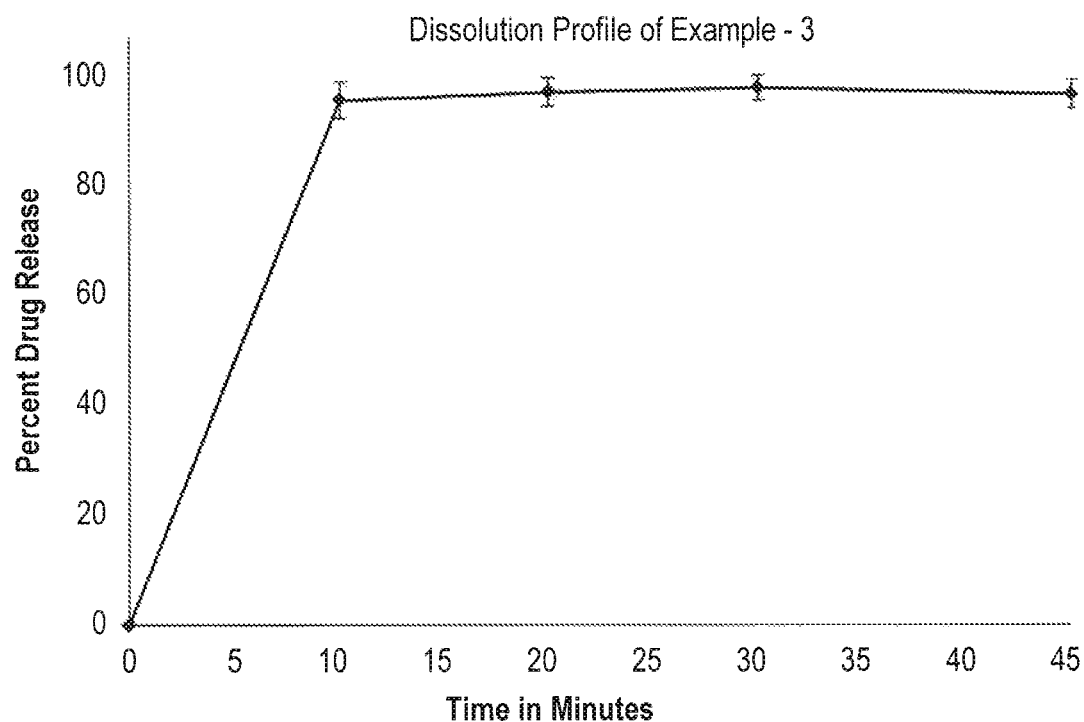
FIG. 10 is a graph illustrating the mean dissolution profile of formulations prepared in accordance with Example 3.
Figure 11:
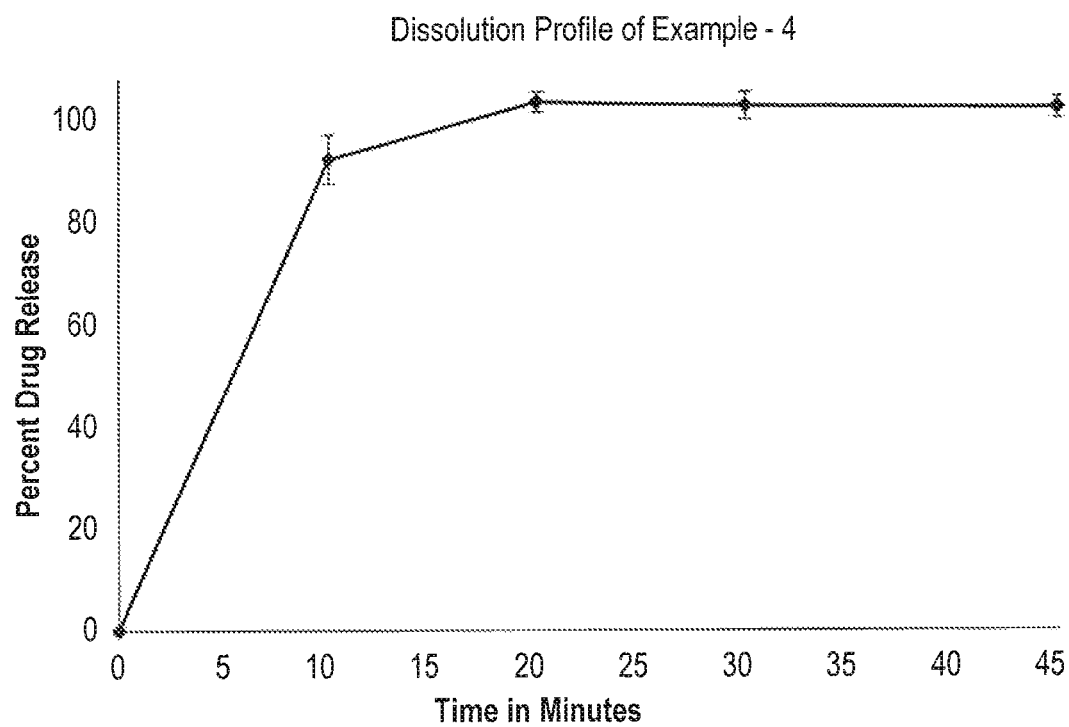
FIG. 11 is a graph illustrating the mean dissolution profile of formulations prepared in accordance with Example 4.
Figure 12:
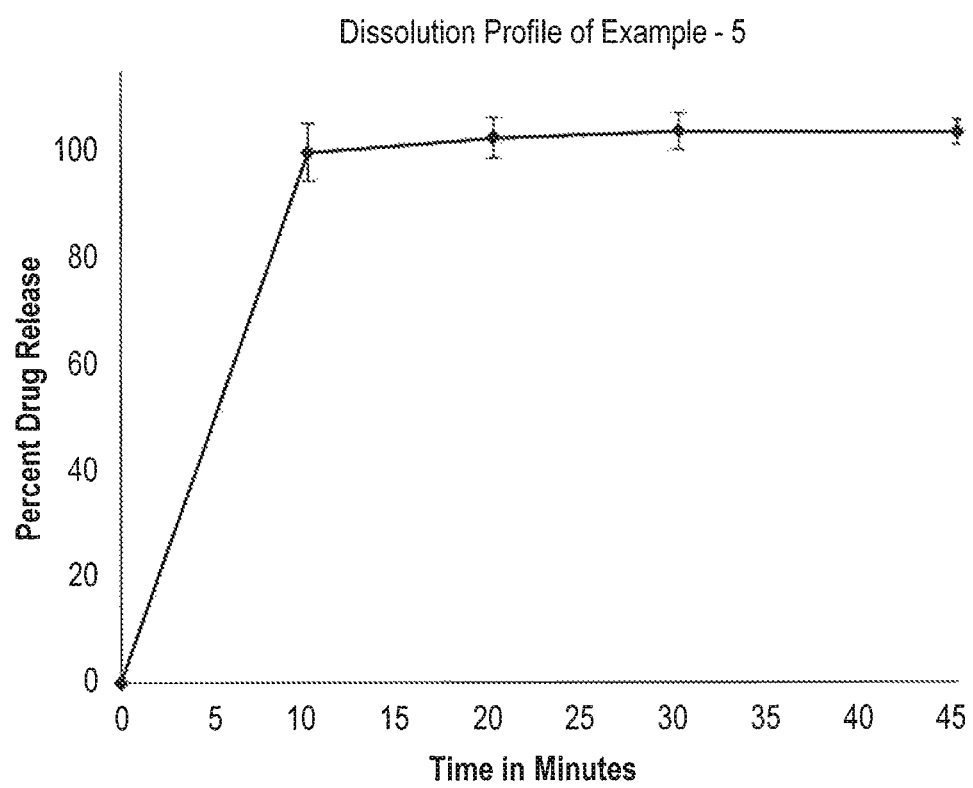
FIG. 12 is a graph illustrating the mean dissolution profile of formulations prepared in accordance with Example 5.

Method-VII is illustrated in FIG. 7. Method-VII includes four steps:
- Step-I: Dissolving the drug substance in a suitable vehicle to create a drug solution;
- Step-II: Filling non-therapeutic material into the capsule body;
- Step-III: Transferring the required volume of drug solution into non-therapeutic material filled in the capsule body; and
- Step-IV: Closing the capsule body using a capsule cap.

The following Examples show exemplary implementations of the methods according to the above embodiments of the present subject matter.

EXAMPLE 1

Low Dose Pharmaceutical Formulation of Desmopressin (120 µg)

Desmopressin acetate (equivalent to 5 mg desmopressin base) was dissolved in a 1.0 ml ethanol (rug solution). Twenty-four microliters (24 µl) of the drug solution was transferred into a capsule body with a corresponding capsule cap removed. The solvent of the drug solution was removed from the capsule body by drying at room temperature for 24 hours. After 24 hours, a mixture of mannitol and crospovidone (90:10% w/w) was filled in the capsule body. The capsule body was closed by placing the capsule cap over it.

EXAMPLE 2

Low Dose Pharmaceutical Formulation of Desmopressin (120 µg)

Desmopressin acetate (equivalent to 5 mg desmopressin base) was dissolved in 1.0 ml ethanol. A mixture of mannitol and crospovidone (90:10% w/w) was filled in a capsule body. The capsule body was closed by placing a capsule cap over it. A needle of a 1 ml syringe was fixed on the tip cone of a micropipette. Twenty-four microliters (24 µl) of the drug solution was sucked into a liquid chamber of the needle with the help of the micropipette. The solution was injected into the mannitol and crospovidone (90:10% w/w) mixture filled in the shell.

EXAMPLE 3

Low Dose Pharmaceutical Formulation of Desmopressin (120 µg)

Desmopressin acetate (equivalent to 5 mg desmopressin base) was dissolved in 1.0 ml ethanol. Placebo sugar spheres were disposed in the capsule body. The capsule body was closed by placing the capsule cap over the opening. A needle of a 1 ml syringe was fixed on the tip cone of a micropipette. Twenty-four microliters (24 µl) of a drug solution was sucked into the liquid chamber of the needle with the help of a micropipette. The solution was injected into the capsule shell filled with placebo sugar spheres.

EXAMPLE 4

Low Dose Pharmaceutical Formulation of Desmopressin (60 µg)

Desmopressin acetate (equivalent to 5 mg desmopressin base) was dissolved in 1.0 ml ethanol. Twelve-microliters (12 µl) of drug solution was transferred into a capsule body. The solvent of the drug solution was removed from the capsule body by drying at room temperature for 12 hours. After 12 hours, the mixture of mannitol and crospovidone (90:10% w/w) was filled in the capsule body. The capsule body was closed by placing the capsule cap over it.

EXAMPLE 5

Low Dose Pharmaceutical Formulation of Desmopressin (60 µg)

Desmopressin acetate (equivalent to 5 mg desmopressin base) was dissolved in 1.0 ml ethanol. Twelve-microliters (12 µl) of drug solution was transferred into a capsule body. The solvent of the drug solution was removed from the capsule body by drying at room temperature for 12 hours. After 12 hours, the capsule body was closed by placing the capsule cap over the opening.

EXAMPLE 6

Low Dose Pharmaceutical Formulation of Desmopressin (130 µg)

Desmopressin acetate (equivalent to 5 mg desmopressin base) was dissolved in 1.0 ml ethanol. The mixture of mannitol and crospovidone (90:10% w/w) was filled in the capsule body. The capsule body was closed by placing the capsule cap over the opening. A needle of 1 ml syringe was fixed on the tip cone of the micropipette. Twenty-six microliter (26 µl) of drug solution was sucked into the liquid chamber of the needle with the help of a micropipette. The solution was injected into the mannitol and crospovidone (90:10% w/w) mixture in the capsule shell by piercing the capsule cap with the needle.

EXAMPLE 7

Low Dose Formulations of Desmopressin (120 µg)

Desmopressin acetate (equivalent to 5 mg desmopressin base) was dissolved in 1.0 ml ethanol. Three carrier discs (formed from Whatman® filter paper Grade 3, using a hole puncher) were placed in the capsule body. Twenty-four microliters (24 µl) of drug solution was transferred over carrier discs inside the capsule body. The solvent of drug solution was removed from the discs in the capsule body by overnight drying at room temperature. After drying, the capsule body was closed by placing the capsule cap over it.

Dissolution tests were performed on the low dose pharmaceutical formulations prepared according to Examples 1-5. The dissolution of exemplary low dose formulations prepared according to examples 1-5 was performed in water (500 mL), maintained at 37±0.5° C., using a USP IInd apparatus (2016 U.S. Pharmacopoeia-National Formulary [USP 39 NF 34]. 1 Rockville, Md.: United States Pharmacopeial Convention, Inc, 2016. [711] Dissolution). The paddles were rotated at 75 rpm, and the samples were withdrawn at 10, 20, 30, and 45 minute time intervals. The samples were filtered using Chromafil® Xtra PTFE-45/25 0.45 µm syringe filter. The filtered samples were analyzed, without any further processing. The percent drug release over time for the formulations described in Examples 1-5 are shown in FIGS. 8-12, respectively. The dissolution tests showed that the exemplary low dose pharmaceutical formulations prepared according to the exemplary methods described above each met the standard of immediate release formulations.

Content Uniformity of Low Dose Formulations of Desmopressin

The capsules of formulations prepared according to examples 1 and 7 were analyzed for content uniformity. Ten capsules were sampled and each capsule was placed in a separate 500 ml volumetric flask, and then 100 ml water (maintained at 37° C.±1) was filled in each flask. Each flask was shaken vigorously until the capsule therein disintegrated. The volume of each flask was adjusted up to 500 ml with water. Each flask was then sonicated for 20 minutes in a sonication bath. Each flask was then allowed to cool to room temperature. A sample was withdrawn from each flask and filled in a neutral graduated micro test tube (1.5 mL, capacity, conical tubes). The test tubes were centrifuged at 13000 rpm for 10 minutes. After centrifugation, the supernatant was withdrawn and analyzed using UPLC-MS/MS method.

The methods of preparing low dose pharmaceutical formulations achieve content uniformity as defined herein, by meeting the content uniformity tests in the U.S. Pharmacopoeia (USP) (2016 U.S. Pharmacopoeia-National Formulary [USP 39 NF 34]. 1 Rockville, Md.: United States Pharmacopeial Convention, Inc, 2016:736-40. [905]Uniformity of Dosage Units). To determine content uniformity, the following analysis was performed: determine the amount of drug in the samples of 10 unit dosage forms; calculate the mean drug content; determine whether the content of each individual unit dosage form falls within a specified limit in terms of % deviation (e.g., 15%) from the mean (i.e., between 85-115% of the calculated mean), and the Relative Standard Deviation (RSD) is less than or equal to 6%. If each individual unit dosage form sampled meets the above criteria, then the content uniformity is achieved. If not, the analysis is repeated using an additional 20 unit dosage forms. If not more than one unit dosage form of the total 30 is outside the range of 85%-115% of the calculated mean, and no unit is outside the range of 75%-125% of the calculated mean and a RSD of the 30 units does not exceed 7.8%, then content uniformity is achieved.

The total 10 capsules from batches of Example 1 and Example 7 were sampled and analyzed for content uniformity, the results are presented in Table 1.

TABLE 1

Results of Content uniformity of Low dose formulations of desmopressin (Target value 120 µg) Example 1 and 7

| Capsule | Drug Content µg/Capsule | Percent Target Value |
|---|---|---|
| 1 | 123.66 | 103.05 |
| 2 | 126.43 | 105.35 |
| 3 | 124.90 | 104.08 |
| 4 | 125.84 | 104.86 |
| 5 | 128.08 | 106.73 |
| 6 | 129.45 | 107.87 |
| 7 | 123.75 | 103.12 |
| 8 | 131.07 | 109.22 |
| 9 | 125.95 | 104.95 |
| 10 | 126.88 | 105.73 |
| Mean | 126.60 | 105.50 |
| SD | 2.37 | 1.98 |
| RSD | 1.87 | 1.87 |

Sample Analysis: Desmopressin was eluted on an Acquity UPLC®BEH C18 1.7 µm, 2.1×50 mm column. The column temperature was maintained at 40±5° C. using column heater. The mobile phase comprised component A [acetonitrile (0.1% formic acid)] and component B [water (0.1% formic acid)]. Mobile phase composition comprised component A and component B in a ratio of 25:75 v/v, Mobile phase composition was pumped in isocratic elution mode at the rate of 300 µL/min. The 10 µL sample was injected and the temperature of auto-sampler was kept at 20±3° C. Sample run time for chromatographic Method was 1.0 min, and the desmopressin was eluted at 0.59 min.

Mass Spectrometer Parameters: Desmopressin ($C_{46}H_{64}N_{14}O_{12}S_2$) was determined using Waters® TQD mass spectrometer. TQD was operated in positive electrospray ionization (ESI$^+$) mode. The precursor ion of desmopressin was selected at m/z 535.33. The daughter fragment of desmopressin (m/z 535.33>120) was monitored in multiple reaction monitoring mode. The cone voltage and collision energy for m/z 535.33>120 transition were 21V and 35 V, respectively. Capillary voltage, extractor voltage, and RF lens were set at 3.4 (kV), 3.0 (V), and 0.1 (V), respectively. The source temperature and desolvation temperature were set at 150° C. and 350° C., respectively. Flow rate of desolvation gas (nitrogen) was 600 L/H. Collision gas (Argon) was applied at 0.12 mL/min. Low mass resolution (LMR1) and high mass resolution (HMR1) were set as 9.2 and 15, while the low mass resolution (LM2 R2) and high mass resolution (HMR2) for MS/MS were 10.6 and 15, respectively. The ion energy (IE1) and (IE2) were set as 0.3 and 1.0, respectively.

It is to be understood that the low dose pharmaceutical formulations and methods of making thereof are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of preparing a content uniform low dose solid pharmaceutical formulation, consisting of sequential steps of:

providing a capsule shell having a capsule body and a capsule cap, the capsule body having an opening at one end;

filling the capsule body with at least one non-therapeutic material; dissolving a drug substance in a solvent to form a drug solution outside of the capsule body, wherein the drug substance defines a dosage equal to or less than 2000 µg;

transferring a portion of the drug solution into the capsule body;

removing the solvent from the drug solution; and closing the opening the capsule body with the capsule cap.

2. The method of preparing the content uniform low dose pharmaceutical formulation of claim 1, wherein the solvent is removed by application of an air stream.

3. The method of preparing the content uniform low dose pharmaceutical formulation of claim 1, wherein the solvent is removed by application of a nitrogen gas stream.

4. The method of preparing the content uniform low dose pharmaceutical formulation of claim 1, wherein the solvent is removed by exposure to air at room temperature.

5. The method of preparing the content uniform low dose pharmaceutical formulation of claim 1, wherein the at least one non-therapeutic material is adsorptive or absorptive.

6. The method of preparing the content uniform low dose pharmaceutical formulation of claim 1, wherein the drug solution is transferred by injection into the capsule shell.

7. The method of preparing the content uniform low dose pharmaceutical formulation of claim 1, wherein the at least one non-therapeutic material is selected from the group consisting of pharmaceutical excipients, placebo granules and sugar spheres.

\* \* \* \* \*